United States Patent
De Roose et al.

(10) Patent No.: US 12,279,911 B2
(45) Date of Patent: Apr. 22, 2025

(54) ULTRASOUND TRANSDUCER AND A SYSTEM

(71) Applicant: IMEC VZW, Leuven (BE)

(72) Inventors: Florian De Roose, Rumst (BE); Kris Myny, Heusden-Zolder (BE)

(73) Assignee: IMEC VZW, Leuven (BE)

( * ) Notice: Subject to any disclaimer, the term of this patent is extended or adjusted under 35 U.S.C. 154(b) by 97 days.

(21) Appl. No.: 18/042,243

(22) PCT Filed: Jul. 1, 2021

(86) PCT No.: PCT/EP2021/068231
§ 371 (c)(1),
(2) Date: Feb. 20, 2023

(87) PCT Pub. No.: WO2022/037833
PCT Pub. Date: Feb. 24, 2022

(65) Prior Publication Data
US 2023/0309966 A1    Oct. 5, 2023

(30) Foreign Application Priority Data
Aug. 21, 2020 (EP) .................................... 20192148

(51) Int. Cl.
*A61B 8/00*   (2006.01)
(52) U.S. Cl.
CPC .......... *A61B 8/4494* (2013.01); *A61B 8/4488* (2013.01); *A61B 8/4281* (2013.01)
(58) Field of Classification Search
CPC ... A61B 8/4494; A61B 8/4488; A61B 8/4281; B06B 2201/55; B06B 1/0207; B06B 1/0629; G10K 11/341
See application file for complete search history.

(56) References Cited

U.S. PATENT DOCUMENTS

| 6,836,159 B2 | 12/2004 | Wodnicki |
| 2004/0174203 A1* | 9/2004 | Wodnicki ........... H03K 17/6874 327/427 |

(Continued)

FOREIGN PATENT DOCUMENTS

WO    2017066612 A1    4/2017

OTHER PUBLICATIONS

European Search Report and Search Opinion, Application No. EP 20192148.3, mailed May 21, 2021, 11 pages.

(Continued)

*Primary Examiner* — Alexei Bykhovski
(74) *Attorney, Agent, or Firm* — McDonnell Boehnen Hulbert & Berghoff LLP

(57) ABSTRACT

This patent disclosure relates to an ultrasound transducer including an array of ultrasound transducing elements, a plurality of transducer drive lines. The ultrasound transducer further includes an array of control circuits, wherein each individual control circuit includes a drive switch and a memory element, the drive switch comprising at least one thin-film transistor, the memory element being configured to store and control the state of the drive switch. The ultrasound transducer further configured so each individual ultrasound transducing element of the array of ultrasound transducing elements has one associated control circuit of the array of control circuits and one associated transducer drive line of the plurality of transducer drive lines, and wherein the ultrasound transducer is configured to, for each individual ultrasound transducing element, drive the individual ultrasound transducing element by the associated transducer drive line when the drive switch of the associated control circuit is in the on-state.

20 Claims, 5 Drawing Sheets

(56) References Cited

U.S. PATENT DOCUMENTS

| | | | |
|---|---|---|---|
| 2005/0057284 A1* | 3/2005 | Wodnicki | B06B 1/0292 |
| | | | 327/100 |
| 2005/0094490 A1 | 5/2005 | Thomenius et al. | |
| 2010/0152587 A1* | 6/2010 | Haider | A61B 8/00 |
| | | | 600/459 |
| 2010/0254550 A1 | 10/2010 | Martin et al. | |
| 2014/0035616 A1* | 2/2014 | Oda | H03K 19/17748 |
| | | | 326/38 |
| 2015/0374335 A1* | 12/2015 | Brown | A61B 8/4488 |
| | | | 367/87 |
| 2022/0152654 A1* | 5/2022 | Cheyns | B06B 1/0622 |

OTHER PUBLICATIONS

PCT International Search Report and Written Opinion, Application No. PCT/EP2021/068231, mailed Dec. 2, 2021, 15 pages.

Kang, Eunchul, Qing Ding, Maysam Shabanimotlagh, Pieter Kruizinga, Zu-Yao Chang, Emile Noothout, Hendrik J. Vos et al. "A Reconfigurable Ultrasound Transceiver ASIC With $24\times40$ Elements for 3-D Carotid Artery Imaging." EEE Journal of Solid-State Circuits 53, No. 7 (2018): 2065-2075.

Kang, Eunchul, Qing Ding, Maysam Shabanimotlagh, Pieter Kruizinga, Zu Yao Chang, Emile Noothout, Hendrik J. Vos et al. "A reconfigurable 24×40 element transceiver ASIC for compact 3D medical ultrasound probes." In ESSCIRC 2017—43rd IEEE European Solid State Circuits Conference, pp. 211-214. IEEE, 2017.

Bailey, D. G., J. A. Sun, A. Meyyappan, G. Wade, and K. R. Erikson. "A computer-controlled transducer for real-time three-dimensional imaging." Acoustical Imaging (1990): 543-552.

* cited by examiner

ULTRASOUND TRANSDUCER AND A SYSTEM

CROSS-REFERENCE TO RELATED APPLICATIONS

The present disclosure is a non-provisional patent application claiming priority to International Patent Application No. PCT/EP2021/068231, filed Jul. 1, 2021, which claims priority to European Patent Application No. EP20192148.3 filed Aug. 21, 2020, the contents of which are hereby incorporated by reference.

FIELD OF THE DISCLOSURE

The present disclosure relates, in general, to ultrasound transducers. More particularly it relates to an ultrasound transducer comprising an array of ultrasound transducing elements.

BACKGROUND

An ultrasound transducer may be used to construct an image of the internal structure of an object. For example, internal organs of a body may be imaged. Ultrasound sound waves from the ultrasound transducer may form an ultrasound signal which is reflected of the internal structure of the object. The ultrasound reflections may then be used to construct the ultrasound image.

Ultrasound transducers are often made using complementary metal-oxide-semiconductor (CMOS) technology. They often comprise an array of ultrasound transducing elements wherein each ultrasound transducing element is associated with a drive circuit that provides an electrical signal. Ultrasound emitted by the various ultrasound transducing elements of the array interfere to form an interference pattern. By controlling the phases of the electrical signals of the individual drive circuits, the interference pattern may be controlled. The ultrasound beam may thereby be shaped or steered. Although conventional ultrasound transducers have many advantages, there is still room for improvement.

SUMMARY

The present disclosure enables a flexible and bendable ultrasound transducer. The present disclosure further enables an ultrasound transducer which provides an ultrasound signal which is adaptable to measurement conditions. The present disclosure further provides a large ultrasound transducer. The present disclosure further provides an inexpensive ultrasound transducer.

Some example embodiments provide an ultrasound transducer for producing an ultrasound signal, the ultrasound transducer comprising:
an array of ultrasound transducing elements; a plurality of transducer drive lines, each transducer drive line being configured to provide an electrical signal capable of driving a subset of the ultrasound transducing elements of the array of ultrasound transducing elements;
an array of control circuits, wherein each individual control circuit of the array of control circuits comprises a drive switch and a memory element, the drive switch being a switch having an on-state and an off-state, the drive switch comprising at least one thin-film transistor, the memory element being configured to store and control the state of the drive switch;
wherein each individual ultrasound transducing element of the array of ultrasound transducing elements has one associated control circuit of the array of control circuits and one associated transducer drive line of the plurality of transducer drive lines, wherein the ultrasound transducer is configured to, for each individual ultrasound transducing element:
drive the individual ultrasound transducing element by the associated transducer drive line when the drive switch of the associated control circuit is in the on-state, such that the individual ultrasound transducing element is activated when the drive switch is in the on-state and the individual ultrasound transducing element is deactivated when the drive switch is in the off-state;
whereby activated ultrasound transducing elements of the array of ultrasound transducing elements function as ultrasound emitters that collectively form the ultrasound signal.

The array of ultrasound transducing elements may be a 2D array of ultrasound transducing elements, e.g. a rectangular 2D array. The array of ultrasound transducing elements may be comprised in a layer. Further, the plurality of transducer drive lines may be comprised in a layer parallel to the layer comprising the array of ultrasound transducing elements.

As each transducer drive line is configured to provide an electrical signal capable of driving a subset of the ultrasound transducing elements, the array of ultrasound transducing elements may be large and cheap. For example, each transducer drive line may provide an electrical signal driving an entire row, or a few rows, e.g. 3 rows, of the array of ultrasound transducing elements. In this example, each ultrasound transducing element may be passed by one single transducer drive line, regardless of how large the ultrasound transducer is, the size of the ultrasound transducer may thereby be unlimited by the number of transducer drive line. In contrast, an ultrasound transducer with one dedicated drive line for each ultrasound transducing element may need to be configured with a large amount of transducer drive lines passing the peripheral ultrasound transducing elements of the array, in order to supply central ultrasound transducing elements of the array with their own transducer drive line. This may require costly high-resolution manufacturing to implement and there may still be a limit to how many transducer drive lines may be fitted over an ultrasound transducing element. Thus, there may be a limit to the total size of the ultrasound transducer.

A large array of ultrasound transducing elements may be particularly useful when the ultrasound transducer operates autonomously, without the influence of a human operator. For example, the ultrasound transducer may be integrated in a patch placed on a body part of a patient for monitoring over an extended period of time. In another example, the ultrasound transducer may be integrated in a sensor which monitors a construction part, e.g. an inaccessible construction part such as a buried pipe, for an extended period of time. While a human operator may move the ultrasound transducer to get the best image, this may not be possible when the ultrasound transducer operates autonomously. However, if the array of ultrasound transducing elements is large enough, a good image may still be acquired. For example, a midwife may move a small ultrasound transducer over the abdomen of a pregnant woman to get a good image of the fetus. A patch comprising an array of ultrasound transducing elements that covers a large part of the abdomen may achieve a similarly good image even if the optimal position was not known when the array of ultrasound transducing elements was placed.

Using the array of control circuits, the ultrasound transducer may be reconfigured depending on the measurement conditions. Some of the ultrasound transducing elements may be activated while others are deactivated, whereby the ultrasound image is formed only by reflections of ultrasound emitted from the activated ultrasound transducing elements. Going back to the example of the midwife; the midwife may move the small ultrasound transducer from the right side of the abdomen to the left side in response to the fetus turning. In an ultrasound transducer according to the invention the ultrasound transducing elements on the right side of the abdomen may be deactivated while the ultrasound transducing elements on the left side are activated. The ultrasound transducer may of course not only be reconfigured in response to a movement, such as the fetus movement. In many applications it may not be known which part of the object is interesting at the time the ultrasound transducer is placed on the object. For example, if it is placed on a buried pipe it may not be known beforehand where cracks will appear in the pipe.

The use of the array of control circuits to activate and deactivate ultrasound transducing elements may mean that the array of ultrasound transducing elements may be made larger. A long transducer drive line, which may be a consequence of a large array of ultrasound transducing elements, may have a significant resistive drop from one end to another if all ultrasound transducing elements associated with the transducer drive line are activated simultaneously. It may therefore not be possible to drive all ultrasound transducing elements associated with the transducer drive line at once, some may need to be deactivated. For example, the ultrasound transducing elements on the right side of the transducer drive line may be deactivated while the ultrasound transducing elements on the left side is activated, or vice versa. In another example every second ultrasound transducing element of the transducer drive line is activated and the remaining ultrasound transducing elements of the transducer drive line are deactivated.

The use of the array of control circuits to activate and deactivate ultrasound transducing elements may save power. For example, if one part of the array of ultrasound transducing elements contribute significantly to the interesting features of the ultrasound image and another part of the array of ultrasound transducing elements contributes less significantly, the ultrasound transducing elements of the less significantly contributing part may be deactivated to save power.

The use of the array of control circuits to activate and deactivate ultrasound transducing elements may improve the image quality. More power may be directed to ultrasound transducing elements that contribute significantly to the interesting features of the ultrasound image by deactivating other ultrasound transducing elements. This may mean that deeper imaging is possible with the ultrasound transducing elements contributing significantly to the interesting features of the ultrasound image. In another example, there may be an element that reflects ultrasound strongly, e.g. a bone of a body part, under one part of the array of ultrasound transducing elements. Such reflected ultrasound may reduce the quality of more interesting parts of the ultrasound image, e.g. parts depicting an organ. By deactivating ultrasound transducing elements in the vicinity of the strongly reflecting element the image quality may be improved.

By implementing each drive switch such that it comprises at least one thin-film transistor the array of control circuits may be made flexible. Further, the array of control circuits may be produced at a low cost when based on thin-film transistors. The production cost per unit area may be low for thin-film transistors.

A thin-film transistor may comprise a thin film of semiconducting material, a source, a drain, and a gate. The gate may control a current from the source to the drain through the thin film. The current may be passed laterally through the thin film.

The thin-film transistor may be free of a semiconducting substrate. The thin-film transistor may instead be attached to a supporting but nonconducting substrate such as an insulating substrate, e.g. a glass substrate, an oxide substrate, or a polymer substrate. The thin-film transistor may be grown or deposited on the substrate.

Semiconducting material in a thin-film transistor may be e.g. amorphous indium-gallium-zinc-oxide (a-IGZO) or other amorphous oxide semiconductors, amorphous silicon, low-temperature polycrystalline silicon (LTPS) or organic semiconducting material.

The structural order of the material of the thin film may be lower than single crystalline structural order. For example, the structural order of the material of the thin-film integrated circuit may be amorphous structural order, microcrystalline structural order, or polycrystalline structural order.

The film thickness of the thin film may depend on the embodiment. In some embodiments the film thickness of the thin-film integrated circuit may lie in a range of 1 nm to 100 μm. In some embodiments the film thickness of the thin-film integrated circuit may lie in a range of 0.5 μm to 50 μm.

Each control circuit of the array of control circuits may be associated with more than one ultrasound transducing element of the array of ultrasound transducing elements. For example, each control circuit of the array of control circuits may be associated with a group of ultrasound transducing elements of the array of ultrasound transducing elements, e.g. 3×3 ultrasound transducing elements. Thus, the number of control circuits may be smaller than the number of ultrasound transducing elements, e.g. a factor 9 smaller.

When an ultrasound transducing element is activated, the drive switch of the control circuit associated with the ultrasound transducing element may close a circuit comprising the ultrasound transducing element and its associated transducer drive line. When an ultrasound transducing element is activated the electrical signal of the associated transducer drive line may flow through the ultrasound transducing element and drive it.

The thin-film transistor of the drive switch may be the component that closes a circuit comprising the ultrasound transducing element and its associated transducer drive line when the drive switch is in the on-state and the ultrasound transducing element is activated.

The memory element may store the state of the drive switch by storing a charge. The memory element may control the state of the drive switch by applying a charge to the gate of the thin-film transistor of the drive switch. The charge stored by the memory element and the charge applied by the memory element to the gate of the thin-film transistor of the drive switch may be the same charge.

The array of control circuits of the ultrasound transducer may be comprised in a thin-film integrated circuit. The thin-film integrated circuit may be configured to form electrical components, wherein at least some of the electrical components are thin-film transistors. The electrical components of the thin-film integrated circuit may further comprise capacitors. Each memory element of each individual control circuit may comprise at least one capacitor of the thin-film integrated circuit. The electrical components of the thin-film integrated circuit may further comprise resistors. The electrical components of the thin-film integrated circuit may further comprise the plurality of transducer drive lines. Alternatively, the plurality of transducer drive lines may be comprised in a separate layer. The separate layer may be adjacent to the thin-film integrated circuit.

The thin-film integrated circuit may at least partially be made of semiconducting material. Thin-film transistors of the thin-film integrated circuit may be made of semiconducting material.

The thin-film integrated circuit may comprise one single semiconductor thin film out of which several, or all, thin-film transistors of the drive switches of the array of control circuits are formed.

The use of thin-film technology in the form of a thin-film integrated circuit may enable production of a large array of control circuits and thereby a large array of ultrasound transducing elements.

The use of thin-film technology in the form of a thin-film integrated circuit may further enable production of a flexible array of control circuits and thereby a flexible ultrasound transducer. Thin-film integrated circuits may further be produced at a low cost in comparison to other integrated circuits. However, the conductivity of components in a thin-film integrated circuit may be lower than the conductivity of an integrated circuit produced using crystalline silicon technology. Accordingly, the thin-film integrated circuit may comprise drive switches such that some of the ultrasound transducing elements may be deactivated.

Further, the resolution of the manufacturing process for a thin-film integrated circuit may be lower than the resolution of the manufacturing process for a crystalline silicon integrated circuit. It may therefore be difficult to fit complex circuitry, such as drive circuitry or phase regulating circuitry, for every ultrasound transducing element or for every group of ultrasound transducing elements, e.g. every 3×3 group of ultrasound transducing elements, onto the thin-film integrated circuit. Complex circuitry, e.g. drive circuitry, may instead be placed outside the array of control circuits.

Each control circuit of the array of control circuits according to the invention may have low complexity and be fitted within a small area even if the resolution of the manufacturing process is low. At the same time, beam steering and/or shaping may still be possible to some extent using the array of control circuits. By activating some ultrasound transducing elements and deactivating other, the interference pattern may be controlled. For example, if each transducer drive line provides an electrical signal driving one, or a few, rows of the array of ultrasound transducing elements, beam steering or beam shaping may be possible in a plane perpendicular to the one or few rows by adjusting the relative phases of the electrical signals of the different transducer drive lines. In a plane parallel to the one or few rows, beam steering or beam shaping, e.g. beam narrowing, may be possible by selectively activating a first subset of the array of ultrasound transducing elements and deactivating a second subset of the array of ultrasound transducing elements. Beam steering or beam shaping may thus be possible in the plane parallel to the one or few rows although possibly at the expense of a reduced resolution in the steered or shaped beam in the plane parallel to the one or few rows. The resolution in the plane parallel to the one or few rows may be unaffected.

The memory element of each individual control circuit of the array of control circuits may be a dynamic random-access memory, DRAM.

The DRAM may consist of a storage capacitor and access switch. The DRAM capacitor may comprise two metal plates separated by a dielectric material. Thus, the DRAM capacitor may be a metal-insulator-metal stack. Alternatively, the DRAM capacitor may comprise a semiconductor plate and a metal plate, separated by a dielectric material. Thus, the DRAM may be a semiconductor-insulator-metal stack. A metal plate of the DRAM may simultaneously function as a gate for a thin-film transistor of the drive switch of the individual control circuit of the array of control circuits.

A DRAM may be a cheap implementation of the memory. The DRAM may be implemented as part of a thin-film integrated circuit. When implemented as part of a thin-film integrated circuit, the DRAM may have lower leakage than when implemented in a single crystalline silicon integrated circuit. Thus, DRAMs may be unsuitable for an array of control circuits implemented in a single crystalline silicon integrated circuit but be very suitable for an array of control circuits implemented in a thin-film integrated circuit.

There are of course alternatives to the DRAM implementation of the memory element of each individual control circuit of the array of control circuits. According to one alternative, the memory element of each individual control circuit of the array of control circuits may be a static random-access memory, SRAM. According to another alternative, the memory element of each individual control circuit of the array of control circuits may be a ferroelectric random-access memory, FeRAM. According to another alternative, the memory element of each individual control circuit of the array of control circuits may be an oxide based random-access memory, OxRAM.

The ultrasound transducer may comprise:
  a plurality of ultrasound transducer drive circuits, each ultrasound transducer drive circuit being a circuit configured to provide the electrical signal capable of driving a subset of the ultrasound transducing elements via one of the plurality of transducer drive lines, the plurality of ultrasound transducer drive circuits being arranged outside the array of ultrasound transducing elements and outside the array of control circuits.

By arranging the plurality of ultrasound transducer drive circuits outside the array of ultrasound transducing elements and outside the array of control circuits the ultrasound transducer drive circuits may be designed separately without considering any restriction on the array of ultrasound transducing elements or the array of control circuits. For example, each ultrasound transducer drive circuit may be larger than one or a few ultrasound transducing elements. If the ultrasound transducer drive circuit does not need to be fitted on the ultrasound transducing element or on the control circuit associated with the ultrasound transducing element, the ultrasound transducer drive circuit may be designed more freely which may save cost. For example, the plurality of ultrasound transducer drive circuits may be implemented as a thin-film integrated circuit. Either as a different thin-film integrated circuit than a thin-film integrated circuit comprising the array of control circuits or on the same thin-film integrated circuit but at a different location from the array of control circuits. Alternatively, the plurality of ultrasound transducer drive circuits may be implemented using a single crystalline silicon integrated circuit or a CMOS circuit.

The plurality of ultrasound transducer drive circuits may be arranged at a lateral position of the array of ultrasound transducing elements and the array of control circuits.

In case the array of ultrasound transducing elements and the array of control circuits are flexible it may be advantageous to arrange the plurality of ultrasound transducer drive circuits at a lateral position such that they do not impede the flexibility. For example, the plurality of ultrasound transducer drive circuits may be implemented as non-flexible or less flexible circuits.

The array of ultrasound transducing elements, and the array of control circuits may thus be flexible, such that the ultrasound transducer can be bent to conform to a curved surface of an object to be examined. Further, the plurality of transducer drive lines may also be flexible. When an ultrasound transducer can conform to a curved surface it may ensure a good contact with the object to be investigated. It may be particularly important for the ultrasound transducer to conform to a curved surface of an object if the array of ultrasound transducer elements is large.

The array of ultrasound transducing elements may be arranged above the array of control circuits. For example, the array of ultrasound transducing elements may be comprised in a layer which is arranged above a layer comprising the array of control circuits. When the array of ultrasound transducing elements is arranged above the array of control circuits each ultrasound transducing element may be arranged in the vicinity of its associated control circuit. Each ultrasound transducer element of the array of ultrasound transducing elements may be arranged above the associated control circuit of the array of control circuits. Alternatively, when a group of ultrasound transducer elements of the array of ultrasound transducing elements is associated with the same control circuit of the array of control circuits, the group of ultrasound transducer elements may be arranged above the control circuit associated with the group of ultrasound transducer elements. What is considered to be above and below is of course a matter of perspective. Thus, in the preceding part of the paragraph the term "above" can equally well be "below".

The array of ultrasound transducing elements may be comprised in a flexible layer, wherein each ultrasound transducing element of the array of ultrasound transducing elements comprise at least one piezo element supported by the flexible layer and one cavity in the flexible layer.

An ultrasound transducing element may thus be driven by the piezoelectric effect. The ultrasound transducing element may emit ultrasound when an AC electric field is applied near or at the resonance frequency of the ultrasound transducing element. The AC electric field may be applied through the electrical signal supplied by the transducer drive line associated with the ultrasound transducing element. The resonance frequency of the ultrasound transducing element may be defined by the dimensions of the cavity. The at least one piezo element may be arranged above or below the cavity.

The array of ultrasound transducing elements may be configured such that all ultrasound transducing elements have the same resonance frequencies. Alternatively, the array of ultrasound transducing elements may comprise two or more subsets of ultrasound transducing elements with different resonance frequencies.

The ultrasound transducing elements may be micromachined ultrasound transducers.

The ultrasound transducing elements may thus be or comprise piezoelectric micromachined ultrasound transducers (pMUTs).

As a further example, the ultrasound transducing elements may be or comprise capacitive micromachined ultrasound transducers (cMUTs).

Each individual control circuit of the array of control circuits may comprise write circuitry, the write circuitry being circuitry configured to write the state of the drive switch of the individual control circuit into the memory element of the individual control circuit.

The write circuitry may be used to reconfigure the ultrasound transducer. The write circuitry may comprise at least one thin-film transistor. The write circuitry of an individual control circuit may comprise a write select line and a write data line. The write select line of the control circuit may be shared with other control circuits of the array of control circuits, e.g. with control circuits within the same row of the array of control circuits. The write data line of the control circuit may be shared with other control circuits of the array of control circuits, e.g. with control circuits within the same column of the array of control circuits. When one row of the array of control circuits is read selected, the states of the drive switches of the control circuits of said row may be simultaneously written through the respective write data lines.

The ultrasound transducer may comprise a first integrated circuit structure configured to set an ultrasound signal pattern of the ultrasound signal by, for each individual control circuit of the array of control circuits:

writing the state of the drive switch of the individual control circuit into the memory element of the individual control circuit to either activate or deactivate the ultrasound transducing element associated with the individual control circuit, such that the activated ultrasound transducing elements of the array of ultrasound transducing elements emit the ultrasound signal in the ultrasound signal pattern.

The first integrated circuit structure may be arranged at a lateral position of the array of ultrasound transducing elements and the array of control circuits.

The ultrasound transducer may comprise a plurality of transducer readout lines, each individual transducer readout line of the plurality of transducer readout lines being configured to be connectable to at least one ultrasound transducing element of the array of ultrasound transducing elements and to output an electrical signal generated by absorption of an ultrasound signal in ultrasound transducing elements that are connected to the individual transducer readout line. Thus, ultrasound transducing elements of the array of ultrasound transducing elements may be used to detect a reflected ultrasound signal. For example, deactivated ultrasound transducing elements of the array of ultrasound transducing elements may be used as detectors. Consequently, which ultrasound transducing elements are used as emitters and which are used as detectors need not be predefined but can be defined dependent on the measurement conditions. It may save cost not to have one group of ultrasound transducing elements that are always being dedicated as emitters and another group of ultrasound transducing elements that are always being dedicated as detectors. Instead the function of an ultrasound transducing element may be changed dynamically. This may be particularly useful if all ultrasound transducing elements cannot be powered, and used as emitters, simultaneously. Then the remaining deactivated ultrasound transducing elements, or a subset of the remaining deactivated ultrasound transducing elements, may instead be used as detectors.

Each individual control circuit of the array of control circuits may have one associated transducer readout line of the plurality of transducer readout lines and each individual control circuit may comprise a transducer readout switch, the transducer readout switch being a switch with an on-state and an off-state, the on-state of the transducer readout switch connecting the ultrasound transducing element associated with the individual control circuit to the transducer readout line associated with the individual control circuit, whereby the connected ultrasound transducing element is readout selected;

the off-state of the transducer readout switch disconnecting the ultrasound transducing element associated with the individual control circuit from the transducer readout line associated with the individual control circuit, whereby the disconnected ultrasound transducing is readout deselected.

Thus, an individual transducer readout line of the plurality of transducer readout lines may be connectable to one or more ultrasound transducing elements via the respective readout switch associated with the one or more ultrasound transducing elements.

When a transducer readout line is connectable to more than one ultrasound transducing element the ultrasound transducer may be configured to connect only one of the ultrasound transducing elements at a time to the transducer readout line. Thus, conflicting signals from different ultrasound transducing elements may be prevented from entering the transducer readout line simultaneously. Alternatively, the ultrasound transducer may be configured to connect a subset of the ultrasound transducing elements at a time to the transducer readout line, the subset being neighboring ultrasound transducing elements. Thus, the subset of ultrasound transducing elements may act together as one detector and increase the detected signal.

The transducer readout switch may comprise at least one thin-film transistor.

The ultrasound transducer may comprise a second integrated circuit structure configured to readout select ultrasound transducing elements of the array of ultrasound transducing elements by setting the transducer readout switches of the control circuits associated with the readout selected ultrasound transducing elements in the on-state.

The second integrated circuit structure may be arranged at a lateral position of the array of ultrasound transducing elements and the array of control circuits.

According to the above, an ultrasound transducing element of the array of ultrasound transducing elements may function either as an emitter or a detector. However, another approach with a first array of ultrasound transducers always acting as emitters, wherein specific ultrasound transducing elements may be activated or deactivated, and a second array of ultrasound transducers always acting as detectors, may of course also be used. Ultrasound transducers of the second array of ultrasound transducers may of course be readout selected or deselected analogously to what is described above. The first and second array of ultrasound transducers may be interlaced. The first and second array of ultrasound transducers may be implemented in the same layer. Control circuits associated with ultrasound transducers of the first array of ultrasound transducers may be interlaced with control circuits associated with ultrasound transducers of the second array of ultrasound transducers. Control circuits associated with ultrasound transducers of the first array of ultrasound transducers may be implemented in the same layer as control circuits associated with ultrasound transducers of the second array of ultrasound transducers.

In some example embodiments, there is provided a system comprising an ultrasound transducer with a first integrated circuit structure and a processor, wherein the processor is configured to calculate which of the ultrasound transducing elements of the array of ultrasound transducing elements to be activated by the first integrated circuit structure, the calculation ensuring that a power drawn by one or more of the plurality of transducer drive lines is below a power threshold, the power threshold being a maximum electrical power the one or more of the plurality of transducer drive lines is allowed to draw.

The calculation may ensure that the power drawn by one single transducer drive line is below a power threshold. For example, the calculation may ensure that no more than a threshold number of ultrasound transducing elements associated with the transducer drive line are activated simultaneously, the threshold number being such that the power threshold is not exceeded.

The calculation may ensure that the power drawn by the entire plurality of transducer drive lines is below a power threshold. For example, the calculation may ensure that no more than a threshold number of ultrasound transducing elements of the plurality of ultrasound transducing elements are activated simultaneously, the threshold number being such that the power threshold is not exceeded.

In some example embodiments, there is provided a system comprising an ultrasound transducer with a first integrated circuit structure and a processor, wherein the processor is configured to calculate which of the ultrasound transducing elements of the array of ultrasound transducing elements to be activated by the first integrated circuit structure, the calculation ensuring that a backscattering of the ultrasound signal is below a backscattering threshold, the backscattering of the ultrasound signal being a part of the ultrasound signal that is backscattered into a region of the ultrasound transducer, the backscattering threshold being a maximum ultrasound power that is allowed to be backscattered into the region.

The calculation may ensure that a backscattering of the ultrasound signal is below a backscattering threshold by deactivating ultrasound transducing elements that create a large backscattering signal, e.g. due to a strong ultrasound reflector close to the surface of sensor. For example, if a first ultrasound transducing element, when activated, creates a backscattering signal above the power threshold in the region of a second ultrasound transducing element or in the region of a group of ultrasound transducing elements, the calculation may ensure that the first ultrasound transducing element is deactivated.

BRIEF DESCRIPTION OF THE DRAWINGS

The above, as well as additional objects, features and advantages of the present inventive concept, will be better understood through the following illustrative and non-limiting detailed description, with reference to the appended drawings. In the drawings like reference numerals will be used for like elements unless stated otherwise.

DETAILED DESCRIPTION

In cooperation with attached drawings, the technical contents and detailed description of the present disclosure are described thereinafter according to one or more preferable embodiments, being not used to limit the claimed scope. This disclosure may be embodied in many different forms and should not be construed as limited to any one of the embodiments set forth herein; rather, these embodiments are provided for thoroughness and completeness, and fully convey the scope of the invention to the skilled person.

Figure 1:
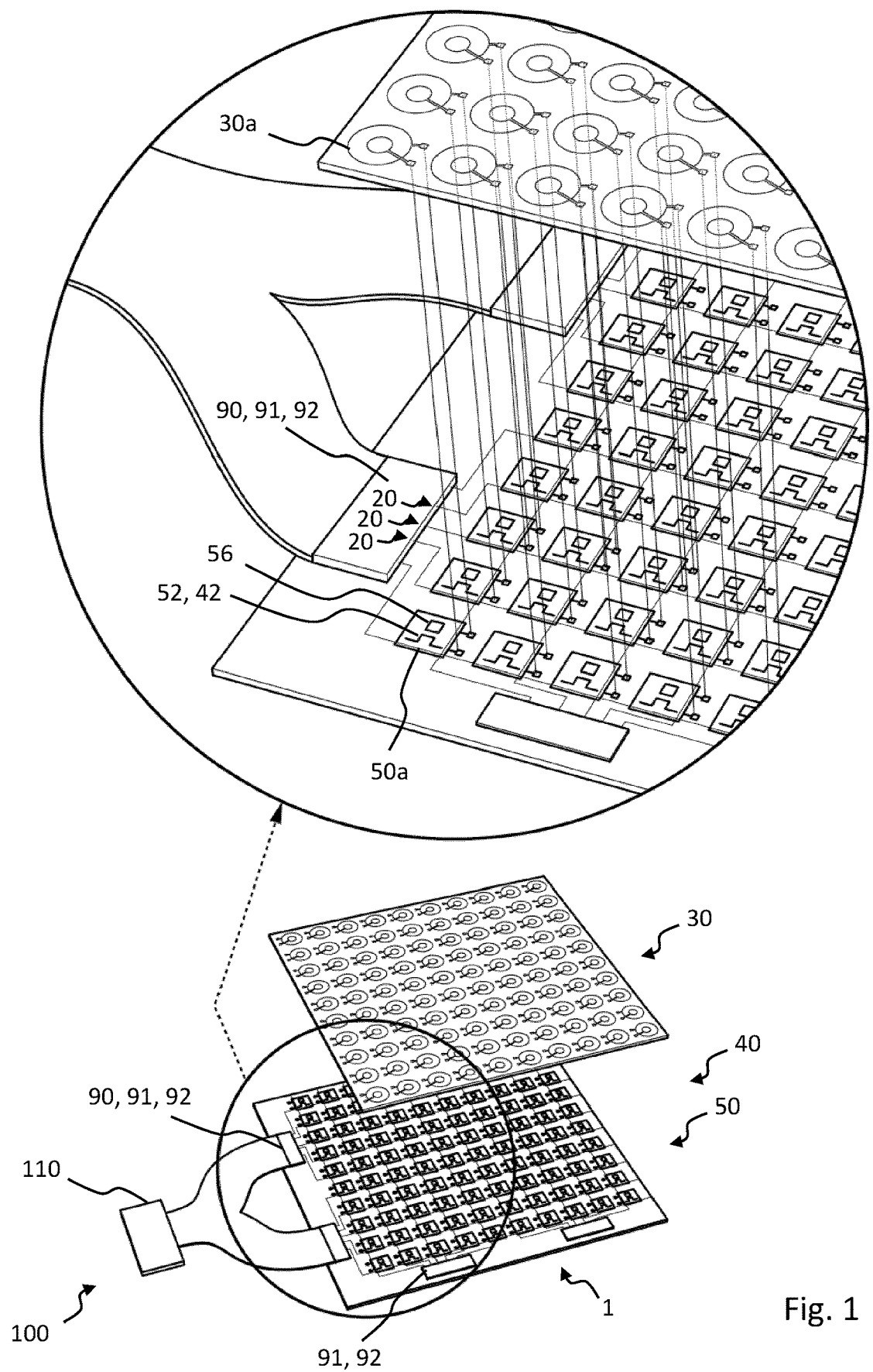
FIG. 1 illustrates a system comprising an ultrasound transducer, in some example embodiments.

FIG. 1 illustrates a system 100 comprising an ultrasound transducer 1. The ultrasound transducer 1 comprises an array 30 of ultrasound transducing elements 30a, a plurality of transducer drive lines 20 and an array 50 of control circuits 50a.

The array 30 of ultrasound transducing elements 30a may be comprised in a layer. The array 50 of control circuits 50a may also be comprised in a layer. The array 30 of ultrasound transducing elements 30a and the array 50 of control circuits 50a may be comprised in parallel layers, as illustrated in FIG. 1. Thus, the array 30 of ultrasound transducing elements 30a may be arranged above the array 50 of control circuits 50a, as further illustrated in FIG. 1. A layer comprising an array 30 of ultrasound transducing elements 30a may be adjacent to, or attached to, a layer comprising an array 50 of control circuits 50a. In FIG. 1 the layers are separated for illustrative purposes. Further, in the figure the array 50 of control circuits 50a is comprised in a thin-film integrated circuit 40. Thus, a layer comprising an array 50 of control circuits 50a may be a thin-film integrated circuit 40. In FIG. 1, the thin-film integrated circuit 40 further comprises the plurality of drive lines 20. However, the plurality of drive lines 20 may alternatively be arranged in another way, e.g. comprised in a separate layer.

Each transducer drive line 20 is configured to provide an electrical signal capable of driving a subset of the ultrasound transducing elements 30a of the array 30 of ultrasound transducing elements 30a. In FIG. 1 each transducer drive line 20 is connected to all the ultrasound transducing elements 30a of one row of the array 30 of ultrasound transducing elements 30a. However, other connection schemes are also possible. For example, each transducer drive line 20 may be connected to several rows of the array 30, e.g. 3 rows. Each row of the array 30 may, additionally or alternatively, be connected to several transducer drive lines 20. For example, a left part of the row may be connected to one transducer drive line 20 and a right part of the row may be connected to another transducer drive line 20. An ultrasound transducing element 30a connected to a transducer drive line 20 may be considered to be associated with the connected transducer drive line 20.

Figure 2:
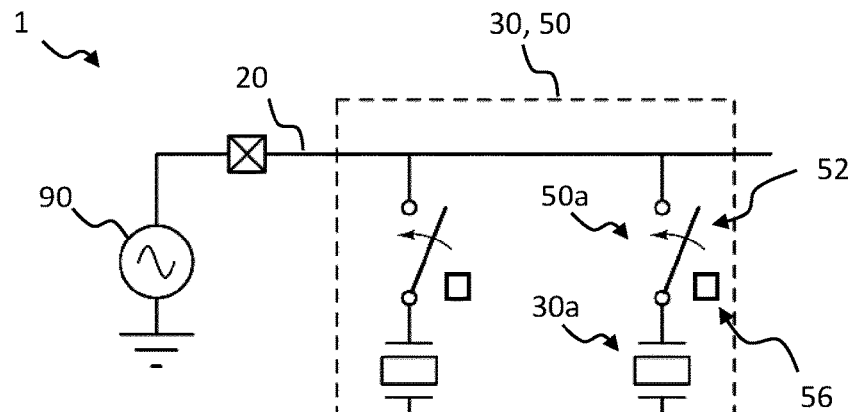
FIG. 2 illustrates an ultrasound transducer, in some example embodiments.

FIG. 2 schematically illustrates a circuit diagram of an ultrasound transducer 1 comprising an 2×2 array 30 of ultrasound transducing elements 30a and an 2×2 array 50 of control circuits 50a. The array size in FIG. 2 is small for illustrative purposes. In a real ultrasound transducer 1 array sizes are generally larger. For example, an array 30 of ultrasound transducing elements 30a may comprise 501× 501 ultrasound transducing elements 30a or more, an array 50 of control circuits 50a may comprise 167×167 control circuits 50a or more. Thus, every control circuit 50a may control 3×3 ultrasound transducing elements 30a. Every control circuit 50a controlling 3×3 ultrasound transducing elements 30a may form one pixel. Thus, the ultrasound transducer may have 167×167 pixels. The surface area of an array 30, 50 of ultrasound transducing elements 30a or control circuits 50a may be at least 100 $cm^2$, such as at least 400 $cm^2$.

Both larger and smaller arrays are possible. For example, 32×32 pixels, 64×64 pixels, or 300×300 pixels.

In FIG. 2 each ultrasound transducing element 30a of a row of the 2×2 array 30 of ultrasound transducing elements 30a is connected to the same transducer drive line 20. Further in FIG. 2, each transducer drive line 20 is connected to an ultrasound transducer drive circuit 90 configured to provide an electrical signal to the transducer drive line 20. Thus, the ultrasound transducer drive circuit 90 may drive any ultrasound transducing element 30a it is connected to via the transducer drive line 20. However, the ultrasound transducer drive circuit 90 may not necessarily be able to simultaneously drive all ultrasound transducing elements 30a it is connected to via the transducer drive line 20.

Each ultrasound transducing element 30a may be connected to a control circuit 50a and thereby associated with the control circuit 50a. In FIGS. 1 and 2 each control circuit 50a is connected to one single ultrasound transducing element 30a, and thereby controls said ultrasound transducing element 30a. However, each control circuit 50a may alternatively be connected to a group of ultrasound transducing elements 30a, and thereby control said group of ultrasound transducing elements 30a. For example, each control circuit 50a may be connected to, and control, a 3×3 sub-array of ultrasound transducing elements 30a. A control circuit 50a may be connected to the associated ultrasound transducing element(s) 30a via two contacts, as illustrated in FIG. 1. Alternatively, a control circuit 50a may be connected to the associated ultrasound transducing element(s) 30a via one single contact.

Each control circuit 50a of the array 50 of control circuits 50a comprises a drive switch 52 and a memory element 56, the drive switch 52 being a switch having an on-state and an off-state, the drive switch 52 comprising at least one thin-film transistor 42, the memory element 56 being configured to store and control the state of the drive switch 52. The drive switch 52 may e.g. be a thin-film transistor 42. The drive switch 52 of a control circuit 50a may control whether the ultrasound transducing element 30a, associated with the control circuit 50a, is activated or deactivated. The drive switch 52 being in the on-state may correspond to an activated ultrasound transducing element 30a, while the drive switch 52 being in the off-state may correspond to a deactivated ultrasound transducing element 30a.

Figure 3:
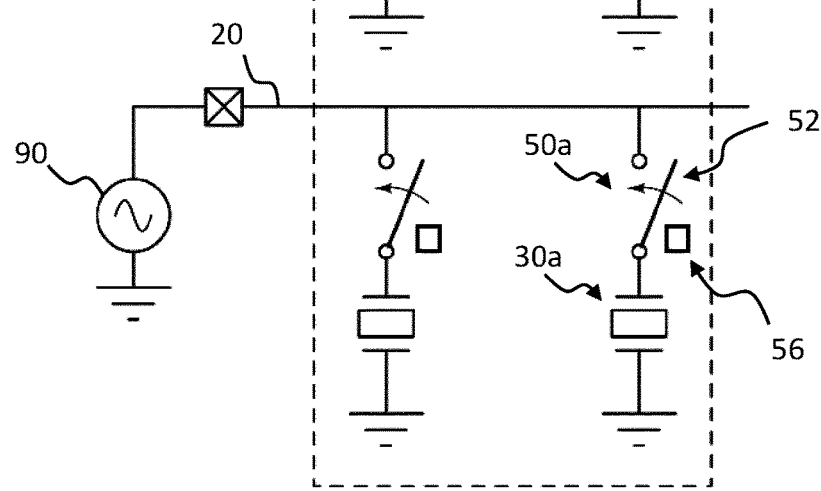
FIG. 3 illustrates an ultrasound transducing element and a control circuit, in some example embodiments.
Figure 3:
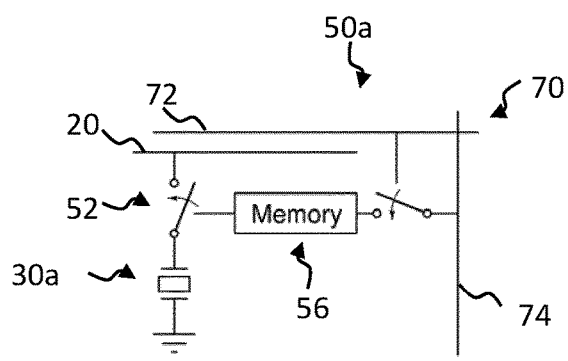
Figure 4:
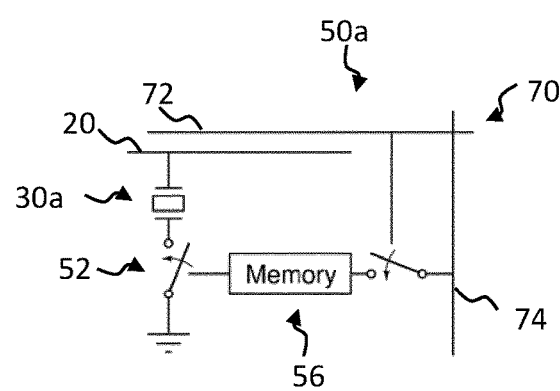
FIG. 4 illustrates an ultrasound transducing element and a control circuit, in some example embodiments.

When an ultrasound transducing element 30a is activated, the drive switch 52 of the control circuit 50a associated with the ultrasound transducing element 30a may close a circuit comprising the ultrasound transducing element 30a and its associated transducer drive line. For example, when an ultrasound transducing element 30a is activated, the drive switch 52 of the control circuit 50a associated with the ultrasound transducing element 30a may connect the ultrasound transducing element 30a with its associated transducer drive line 20, as illustrated in FIG. 3. Alternatively, the ultrasound transducing element 30a may be permanently connected to its associated transducer drive line 20 and when the ultrasound transducing element 30a is activated, the drive switch 52 of the control circuit 50a associated with the ultrasound transducing element 30a instead connects the ultrasound transducing element 30a with ground, thereby closing a circuit comprising the ultrasound transducing element 30a and its associated transducer drive line 20, as illustrated in FIG. 4.

The memory element 56 of a control circuit 50a is configured to store the state of the drive switch 52 of said control circuit 50a. Thus, the ultrasound transducer 1 may be configured and/or reconfigured depending on which states are stored in the memory elements 56 of the control circuits 50a.

A first ultrasound signal pattern may be stored in the memory elements 56 of the ultrasound transducer 1. All ultrasound transducing elements 30a having an associated control circuit 50a with a memory element 56 storing the on-state may then be activated. Said activated ultrasound transducing elements 30a may subsequently emit ultrasound when driven by an electrical signal via a transducer drive line 20. Ultrasound from different activated ultrasound transducing elements 30a may then collectively form an ultrasound signal. The signal pattern of the ultrasound signal may thus be defined, at least partially, by which ultrasound transducing elements 30a are activated. It should be understood that an essential part of defining the ultrasound signal may be how the ultrasound from the various activated ultrasound transducing elements 30a interfere. Defining the signal pattern of the ultrasound signal by activating certain ultrasound transducing elements 30a may comprise beam steering and/or shaping of the ultrasound signal. The ultrasound transducer 1 may emit the first signal pattern until the memory elements 56 are reprogrammed to store a second signal pattern, after which the ultrasound transducer 1 may emit the second signal pattern.

Each individual control circuit 50a of the array 50 of control circuits 50a may comprise write circuitry 70. The write circuitry 70 may write the state of the drive switch 52 of the individual control circuit 50a into the memory element 56 of the individual control circuit 50a. As illustrated in FIGS. 3 and 4 (and also in FIGS. 5-8) the write circuitry 70 may comprise a write select line 72 and a write data line 74. The write select line 72 may select which memory elements 56 should be reprogrammed to store the state defined by the write data line 74.

Figure 5:
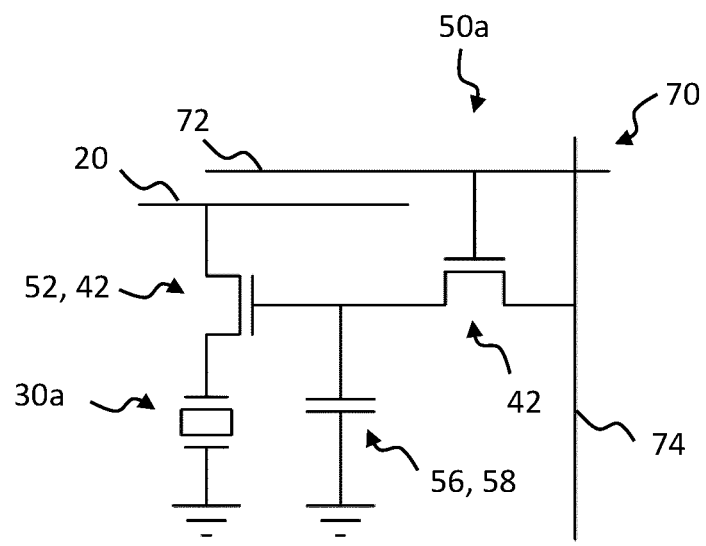
FIG. 5 illustrates an ultrasound transducing element and a control circuit, in some example embodiments.

FIG. 5 illustrates one embodiment of an ultrasound transducing element 30a, its associated control circuit 50a, and its associated transducer drive line 20. The illustrated embodiment may be seen as a DRAM embodiment wherein the memory element 56 may be considered to be a dynamic random-access memory. In FIG. 5 the ultrasound transducing element 30a is connected to ground. The ultrasound transducing element 30a is further connected to the transducer drive line 20 via the drive switch 52, the drive switch in the embodiment being a single thin-film transistor 42. A charge or voltage on the gate of the thin-film transistor 42 of the drive switch 52 may set the drive switch 52 in the on-state and close the circuit comprising the ultrasound transducing element 30a and the associated transducer drive line 20. The ultrasound transducing element 30a may thereby be seen as activated as an electrical signal from the transducer drive line 20 may flow to the ultrasound transducing element 30a. A different charge on the gate of the thin-film transistor 42 may set the drive switch 52 in the off-state and deactivate the ultrasound transducing element 30a.

The charge controlling the voltage at the gate of the drive switch 52 in the figure may be stored in the memory element 56. The memory element 56 in the figure being a DRAM 58. The DRAM 58 may herein be implemented as a thin-film capacitor 44. The control circuit 50a further comprises write circuitry 70 comprising a write select line 72, a write data line 74, and a thin-film transistor 42. In the figure a bias on the write select line 72 may control the gate of the thin-film transistor 42 of the write circuitry 70. A bias on the write select line 72 may thereby allow a write signal on the write data line 74 to be applied to the memory element 56, resulting in a charge being stored in the memory element 56. In the figure, this may charge the thin-film capacitor 44 and said charge may remain, at least for some time, after the gate of the thin-film transistor 42 of the write circuitry 70 has been closed and the memory element 56 has been electrically isolated from the write data line 74. A memory element 56 of the DRAM 58 type may need to be periodically refreshed.

Figure 6:
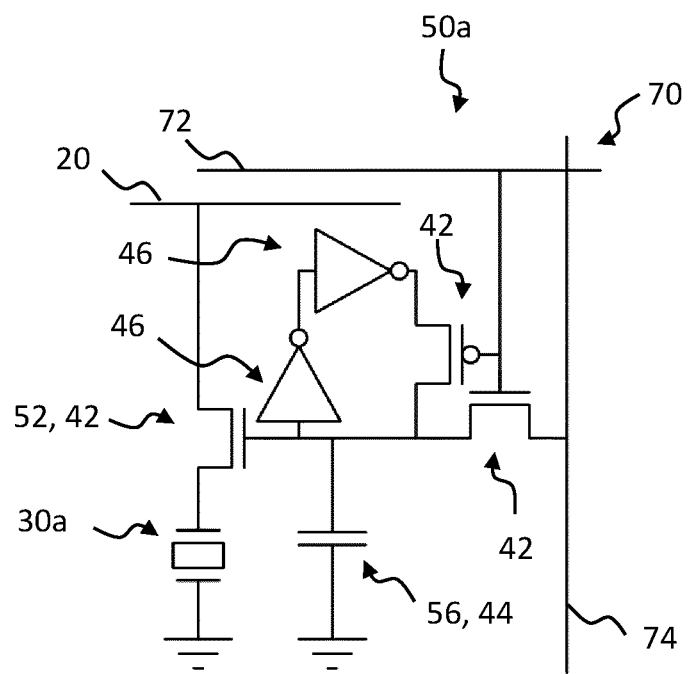
FIG. 6 illustrates an ultrasound transducing element and a control circuit, in some example embodiments.

FIG. 6 illustrates one embodiment of an ultrasound transducing element 30a, its associated control circuit 50a, and its associated transducer drive line 20. The illustrated embodiment may be seen as a DRAM embodiment with bleeder or a static random-access memory (SRAM) embodiment. In addition to the elements described in conjunction with FIG. 5 the embodiment in FIG. 6 comprise a further thin-film transistor 42 and two thin-film inverters 46. In such an embodiment the memory element 56 may not need to be refreshed as often as in the embodiment of FIG. 5. This embodiment may be particularly useful when the thin-film transistors 42 are LTPS thin-film transistors.

Figure 7:
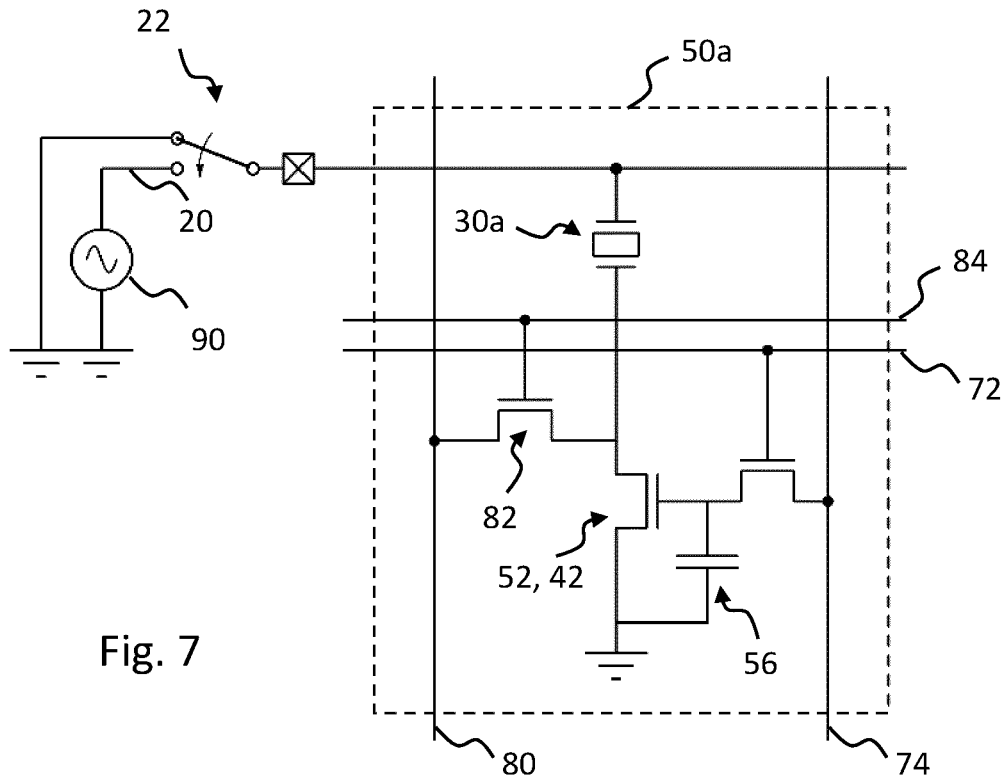
FIG. 7 illustrates an ultrasound transducing element and a control circuit, in some example embodiments.

The ultrasound transducer 1 may be configured such that ultrasound transducing elements 30a that are not driven by an electrical signal can absorb reflected ultrasound and thereby detect it. FIG. 7 illustrates one embodiment of an ultrasound transducer 1, for illustrative purposes only one ultrasound transducing element 30a with its associated control circuit 50a and its associated transducer drive line 20 is shown. In this embodiment the ultrasound transducing element 30a may be used for detecting reflected ultrasound when it is not connected to the transducer drive line 20.

In FIG. 7, the control circuit 50a associated with the ultrasound transducing element 30a comprises a transducer readout line 80, a transducer readout switch 82, and a read select line 84. The transducer readout line 80 is connectable to the ultrasound transducing element 30a by the transducer readout switch 82. In the embodiment of FIG. 7 the transducer readout switch 82 is a transistor with an on-state and an off-state, controlled by the transistor gate. In the on-state, the transducer readout switch 82 connects the ultrasound transducing element 30a to the transducer readout line 80, whereby the connected ultrasound transducing element 30a is readout selected. In the off-state, the transducer readout switch 82 disconnects the ultrasound transducing element 30a from the transducer readout line 80, whereby the connected ultrasound transducing element 30a is readout deselected. As illustrated in FIG. 7, the readout switch 82 may be controlled by the read select line 84. In the embodiment of FIG. 7 a bias from the read select line 84 may be applied to the gate of the transistor that is comprised in the readout switch 82 and thereby control the state of the readout switch 82.

In addition to the readout switches 82 the ultrasound transducer 1 may comprise further switches that enable readout of ultrasound transducing elements 30a. For example, as shown in FIG. 7, the ultrasound transducer 1 may comprise an emitter/detector switch 22. The emitter/detector switch 22 may be configured to switch a connection of a transducer drive line 20 from being connected to an ultrasound transducer drive circuit 90, wherein ultrasound transducing elements 30a associated with the transducer drive line 20 may function as emitters, to being connected to a readout circuit, wherein ultrasound transducing elements 30*a* associated with the transducer drive line 20 may function as detectors. Thus, an ultrasound transducing element 30*a* may function as an emitter when its associated drive switch 52 is in the on-state and when its associated transducer drive line 20 is connected to an ultrasound transducer drive circuit 90. Further, an ultrasound transducing element 30*a* may function as a detector when its associated readout switch 82 is in the on-state and when its associated transducer drive line 20 is connected to a readout circuit.

An ultrasound transducer 1 may comprise a plurality of transducer readout lines 80. Each readout line 80 may be connectable to a plurality of ultrasound transducing elements 30*a*. For example, each readout line 80 may be connectable to one column or row of ultrasound transducing elements 30*a* of the array 30 of ultrasound transducing elements 30*a*. Alternatively, each readout line 80 may be connectable to part of a column or row of ultrasound transducing elements 30*a*. For example, at least 16 or at least 84 of ultrasound transducing elements 30*a* of a column or row of the array 30 of ultrasound transducing elements 30*a*.

The ultrasound transducer 1 may be configured to connect less than a threshold number of ultrasound transducing elements 30*a* to the same readout line 80 simultaneously. For example, the ultrasound transducer 1 may be configured to connect up to 16 pixels to the same readout line 80 simultaneously, wherein each pixel comprises 9 or 16 ultrasound transducing elements 30*a*.

The ultrasound transducer 1 may be configured to prevent ultrasound transducing elements 30*a* of the array 30 of ultrasound transducing elements 30*a* being simultaneously activated and readout selected.

Figure 8:
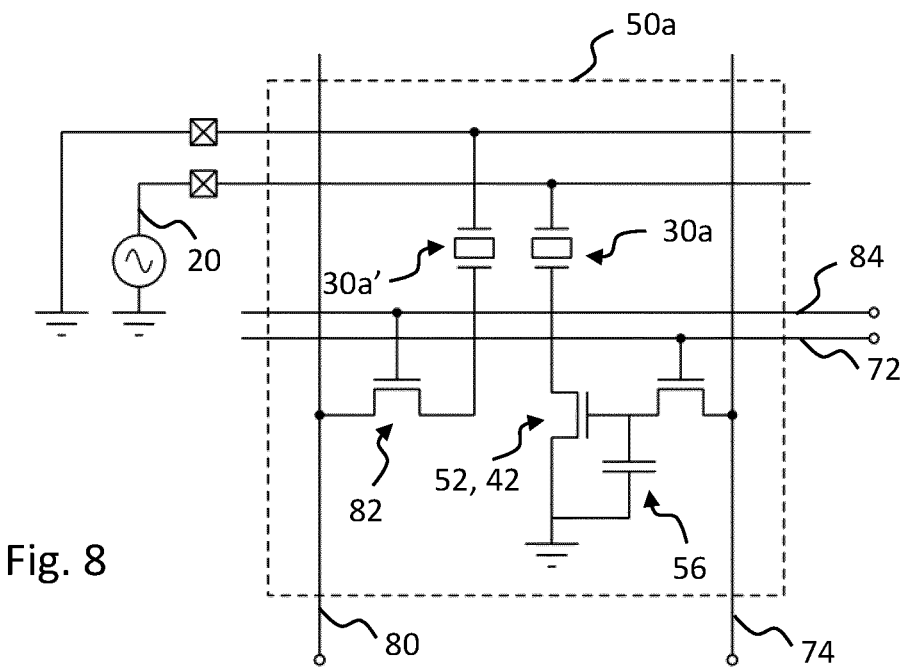
FIG. 8 illustrates an ultrasound transducing element and a control circuit, in some example embodiments.

FIG. 8 shows an alternative embodiment of an ultrasound transducer 1 where a first array 30 of ultrasound transducing elements 30*a* is used as emitters and a second array 30' of ultrasound transducing elements 30*a'* is used as detectors. For illustrative purposes only one ultrasound transducing element 30*a* of the first array 30 is shown, together with its associated control circuit 50*a* and its associated transducer drive line 20, next to one ultrasound transducing element 30*a'* of the second array 30'. Herein the ultrasound transducing element 30*a'* of the second array 30' is connectable to a readout line 80 by transducer readout switch 82 and the readout switch 82 is controlled by a read select line 84 in an analogous manner to the embodiment of FIG. 7.

In addition to the above features the ultrasound transducer 1 may further comprise a first integrated circuit structure 91 configured to set an ultrasound signal pattern of the ultrasound signal by, for each individual control circuit 50*a* of the array 50 of control circuits 50*a*:

writing the state of the drive switch 52 of the individual control circuit 50*a* into the memory element 56 of the individual control circuit 50*a* to either activate or deactivate the ultrasound transducing element 30*a* associated with the individual control circuit 50*a*, such that the activated ultrasound transducing elements 30*a* of the array 30 of ultrasound transducing elements 30*a* emit the ultrasound signal in the ultrasound signal pattern.

The ultrasound transducer 1 may further comprise a second integrated circuit structure 92 configured to readout select ultrasound transducing elements 30*a* of the array 30 of ultrasound transducing elements 30*a* by setting the transducer readout switches 82 of the control circuits 50*a* associated with the readout selected ultrasound transducing elements 30*a* in the on-state.

The first 91 and second 92 integrated circuit structure, as well as the previously mentioned plurality of ultrasound transducer drive circuits 90, may be arranged at one or more lateral positions of the array 30 of ultrasound transducing elements 30*a* and the array 50 of control circuits 50*a*, as shown in FIG. 1. The first 91 and second 92 integrated circuit structure and the plurality of ultrasound transducer drive circuits 90 may be arranged at the edge of a layer comprising the array 50 of control circuits 50*a*. Parts of the first 91 and second 92 integrated circuit structure and the plurality of ultrasound transducer drive circuits 90 may be implemented in one common circuit structure. However, either of the first 91 and second 92 integrated circuit structure and the plurality of ultrasound transducer drive circuits 90 may of course alternatively be implemented in a separate circuit structure.

As previously mentioned, the array 50 of control circuits 50*a* may be comprised in a thin-film integrated circuit 40. Any or all of the first 91 and second 92 integrated circuit structure and the plurality of ultrasound transducer drive circuits 90 may be comprised in one or more CMOS circuits, e.g. application-specific integrated circuits, situated at the edges of the thin-film integrated circuit 40 and connected to the thin-film integrated circuit 40. Further, any or all of the first 91 and second 92 integrated circuit structure and the plurality of ultrasound transducer drive circuits 90 may also be comprised in a thin-film integrated circuit 40, e.g. comprised in the same thin-film integrated circuit 40 as the array 50 of control circuits 50*a*.

As illustrated in FIG. 1, the ultrasound transducer 1 may be part of a system 100 that also comprises a processor 110. The processor 110 may be configured to calculate which of the ultrasound transducing elements 30*a* of the array 30 of ultrasound transducing elements 30*a* should be activated.

In one embodiment, the processor 110 is configured to calculate which of the ultrasound transducing elements 30*a* of the array 30 of ultrasound transducing elements 30*a* to be activated by the first integrated circuit structure 91, the calculation ensuring that a power drawn by one or more of the plurality of transducer drive lines 20 is below a power threshold, the power threshold being a maximum electrical power the one or more of the plurality of transducer drive lines 20 is allowed to draw.

In another embodiment, the processor 110 is configured to calculate which of the ultrasound transducing elements 30*a* of the array 30 of ultrasound transducing elements 30*a* to be activated by the first integrated circuit structure 91, the calculation ensuring that a backscattering of the ultrasound signal is below a backscattering threshold, the backscattering of the ultrasound signal being a part of the ultrasound signal that is backscattered into a region of the ultrasound transducer 1, the backscattering threshold being a maximum ultrasound power that is allowed to be backscattered into the region.

The processor 110 may e.g. receive a desired ultrasound signal pattern, e.g. a region under the ultrasound transducer 1 which should be subjected to the ultrasound signal. The processor 110 may subsequently calculate which of the ultrasound transducing elements 30*a* of the array 30 of ultrasound transducing elements 30*a* to be activated to achieve the desired ultrasound signal pattern while not exceeding the threshold, e.g. not exceeding the power threshold or not exceeding the backscattering threshold.

In one example it may be desired to emit ultrasound from one part, e.g. the right half, of the ultrasound transducer 1 while keeping below a power threshold. If this is achievable, according to the calculation, by activating every second ultrasound transducing element 30*a* on the right half of the array 30 of ultrasound transducing element 30*a*, deactivating the remaining ultrasound transducing elements 30*a* on the right half of the array 30 of ultrasound transducing element 30*a*, and deactivating all ultrasound transducing elements 30*a* on the left half of the array 30 of ultrasound transducing element 30*a*; then the processor 110 may send a command to the first integrated circuit structure 91 to activate/deactivate ultrasound transducing elements 30*a* of the array 30 of ultrasound transducing element 30*a* accordingly.

In another example it may be desired to emit ultrasound from one part, e.g. the top left quadrant, of the ultrasound transducer 1 while keeping backscattering from a bone close to the center of the top left quadrant of the ultrasound transducer 1 below a backscattering threshold. If this is achievable, according to the calculation, by activating every ultrasound transducing element 30*a* in the top left quadrant of the array 30 of ultrasound transducing element 30*a* except for ultrasound transducing elements 30*a* in the vicinity of the bone; then the processor 110 may send a command to the first integrated circuit structure 91 to activate/deactivate ultrasound transducing elements 30*a* of the array 30 of ultrasound transducing element 30*a* accordingly.

The calculations may of course also comprise determining interference between the activated ultrasound transducing elements 30*a*.

Figure 9:
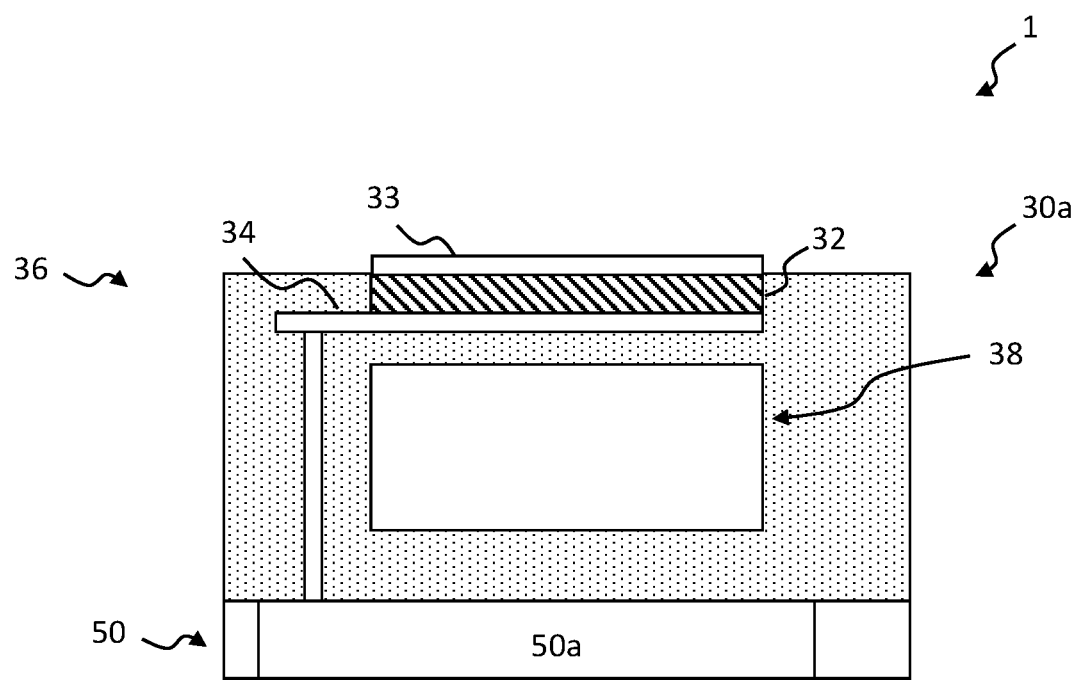
FIG. 9 illustrates an ultrasound transducing element and a control circuit, in some example embodiments.

FIG. 9 illustrates a cross section of an ultrasound transducer 1, for illustrative purposes only one ultrasound transducing element 30*a* with its associated control circuit 50*a* is shown. As illustrated in FIG. 9 the array 30 of ultrasound transducing elements 30*a* may be comprised in a flexible layer 36, wherein each ultrasound transducing element 30*a* of the array 30 of ultrasound transducing elements 30*a* comprise at least one piezo element 32 supported by the flexible layer 36 and one cavity 38 in the flexible layer 36. The piezo element 32 may be arranged between a top contact 33 and a bottom contact 34. At least one of the top contact 33 and the bottom contact 34 may be connected to the associated control circuit 50*a* of the ultrasound transducing element 30*a*. The control circuit 50*a* may thereby activate or deactivate the ultrasound transducing element 30*a*. By applying an AC electric field at the resonance frequency across the piezo element 32, a vibration will be induced and a sound wave emitted. Typical frequencies are in the range of 50 kHz to 20 MHz. This translates into wavelengths ranging from 1 cm down to <100 um.

The flexible layer 36 may be made of a polymer, e.g. polyamide. The array 50 of control circuit 50*a* may be a thin-film integrated circuit 40 that is flexible. The array 50 of control circuit 50*a* may comprise IGZO (Indium Gallium Zinc Oxide) and/or LTPS (Low temperature polysilicon) thin-film transistors 42, at least as drive switches 52.

In the above the inventive concept has mainly been described with reference to a limited number of examples. However, as is readily appreciated by a person skilled in the art, other examples than the ones disclosed above are equally possible within the scope of the inventive concept, as defined by the appended claims.

What is claimed is:

1. An ultrasound transducer for producing an ultrasound signal, the ultrasound transducer comprising:
    an array of ultrasound transducing elements; a plurality of transducer drive lines, each transducer drive line being configured to provide an electrical signal capable of driving a subset of the ultrasound transducing elements of the array of ultrasound transducing elements;
    an array of control circuits, wherein each individual control circuit of the array of control circuits comprises a drive switch and a memory element, the drive switch being a switch having an on-state and an off-state, the drive switch comprising at least one thin-film transistor, the memory element being configured to store and control the state of the drive switch;
    wherein each individual ultrasound transducing element of the array of ultrasound transducing elements has one associated control circuit of the array of control circuits and one associated transducer drive line of the plurality of transducer drive lines, wherein the ultrasound transducer is configured to, for each individual ultrasound transducing element:
        drive the individual ultrasound transducing element by the associated transducer drive line when the drive switch of the associated control circuit is in the on-state, such that the individual ultrasound transducing element is activated when the drive switch is in the on-state and the individual ultrasound transducing element is deactivated when the drive switch is in the off-state;
        whereby activated ultrasound transducing elements of the array of ultrasound transducing elements function as ultrasound emitters that collectively form the ultrasound signal.

2. The ultrasound transducer of claim 1, wherein the memory element of each individual control circuit of the array of control circuits is a dynamic random-access memory, DRAM.

3. The ultrasound transducer of claim 1, the ultrasound transducer further comprising:
    a plurality of ultrasound transducer drive circuits, each ultrasound transducer drive circuit being a circuit configured to provide the electrical signal capable of driving the subset of the ultrasound transducing elements via one of the plurality of transducer drive lines, the plurality of ultrasound transducer drive circuits being arranged outside the array of ultrasound transducing elements and outside the array of control circuits.

4. The ultrasound transducer of claim 1, wherein the array of control circuits is comprised in a thin-film integrated circuit.

5. The ultrasound transducer of claim 4, the ultrasound transducer further comprising:
    a plurality of ultrasound transducer drive circuits, each ultrasound transducer drive circuit being a circuit configured to provide the electrical signal capable of driving the subset of the ultrasound transducing elements via one of the plurality of transducer drive lines, the plurality of ultrasound transducer drive circuits being arranged outside the array of ultrasound transducing elements and outside the array of control circuits.

6. The ultrasound transducer of claim 4, wherein the memory element of each individual control circuit of the array of control circuits is a dynamic random-access memory, DRAM.

7. The ultrasound transducer of claim 1, the ultrasound transducer further comprising:
    a plurality of ultrasound transducer drive circuits, each ultrasound transducer drive circuit being a circuit configured to provide the electrical signal capable of driving the subset of the ultrasound transducing elements via one of the plurality of transducer drive lines, the plurality of ultrasound transducer drive circuits being arranged outside the array of ultrasound transducing elements and outside the array of control circuits.

8. The ultrasound transducer of claim 7, wherein each of the plurality of ultrasound transducer drive circuits is arranged at a lateral position of the array of ultrasound transducing elements and the array of control circuits.

9. The ultrasound transducer of claim 8, wherein the array of ultrasound transducing elements, and the array of control circuits are flexible, such that the ultrasound transducer can be bent to conform to a curved surface of an object to be examined.

10. The ultrasound transducer of claim 1, wherein the array of ultrasound transducing elements, and the array of control circuits are flexible, such that the ultrasound transducer can be bent to conform to a curved surface of an object to be examined.

11. The ultrasound transducer of claim 10, wherein the array of ultrasound transducing elements is arranged above the array of control circuits.

12. The ultrasound transducer of claim 1, wherein the array of ultrasound transducing elements is arranged above the array of control circuits.

13. The ultrasound transducer of claim 1, wherein the array of ultrasound transducing elements is comprised in a flexible layer, wherein each ultrasound transducing element of the array of ultrasound transducing elements comprise at least one piezo element supported by the flexible layer and one cavity in the flexible layer.

14. The ultrasound transducer of claim 1, wherein each individual control circuit of the array of control circuits further comprises write circuitry, the write circuitry being circuitry configured to write the state of the drive switch of the individual control circuit into the memory element of the individual control circuit.

15. The ultrasound transducer of claim 1, the ultrasound transducer further comprising a first integrated circuit structure configured to set an ultrasound signal pattern of the ultrasound signal by, for, each individual control circuit of the array of control circuits:
writing the state of the drive switch of the individual control circuit into the memory element of the individual control circuit to either activate or deactivate the ultrasound transducing element associated with the individual control circuit, such that the activated ultrasound transducing elements of the array of ultrasound transducing elements emit the ultrasound signal in the ultrasound signal pattern.

16. A system comprising the ultrasound transducer of claim 15 and a processor, wherein the processor is configured to calculate which of the ultrasound transducing elements of the array of ultrasound transducing elements to be activated by the first integrated circuit structure, the calculation ensuring that a power drawn by one or more of the plurality of transducer drive lines is below a power threshold, the power threshold being a maximum electrical power the one or more of the plurality of transducer drive lines is allowed to draw.

17. A system comprising the ultrasound transducer of claim 15 and a processor, wherein the processor is configured to calculate which of the ultrasound transducing elements of the array of ultrasound transducing elements to be activated by the first integrated circuit structure, the calculation ensuring that a backscattering of the ultrasound signal is below a backscattering threshold, the backscattering of the ultrasound signal being a part of the ultrasound signal that is backscattered into a region of the ultrasound transducer, the backscattering threshold being a maximum ultrasound power that is allowed to be backscattered into the region.

18. The ultrasound transducer of claim 1, wherein the ultrasound transducer further comprises
a plurality of transducer readout lines, each individual transducer readout line of the plurality of transducer readout lines being configured to be connectable to at least one ultrasound transducing element of the array of ultrasound transducing elements and to output an electrical signal generated by absorption of an ultrasound signal in the at least one ultrasound transducing elements that are connected to the individual transducer readout line.

19. The ultrasound transducer of claim 18, wherein each individual control circuit of the array of control circuits has one associated transducer readout line of the plurality of transducer readout lines and wherein each individual control circuit further comprises a transducer readout switch, the transducer readout switch being a switch with an on-state and an off-state,
the on-state of the transducer readout switch connecting the ultrasound transducing element associated with the individual control circuit to the transducer readout line associated with the individual control circuit, whereby the connected ultrasound transducing element is readout selected;
the off-state of the transducer readout switch disconnecting the ultrasound transducing element associated with the individual control circuit from the transducer readout line associated with the individual control circuit, whereby the disconnected ultrasound transducing element is readout deselected.

20. The ultrasound transducer of claim 19, the ultrasound transducer further comprising a second integrated circuit structure configured to readout select ultrasound transducing elements of the array of ultrasound transducing elements by setting the transducer readout switches of the control circuits associated with the readout selected ultrasound transducing elements in the on-state.

* * * * *